US007501814B2

(12) United States Patent
Thwing et al.

(10) Patent No.: US 7,501,814 B2

(45) Date of Patent: Mar. 10, 2009

(54) APPARATUS AND METHOD FOR SECOND-LAYER THROUGH-BUSHING INSPECTION OF AIRCRAFT WING ATTACHMENT FITTINGS USING ELECTRIC CURRENT PERTURBATION

(75) Inventors: Clinton J. Thwing, Bulverde, TX (US); Gary L. Burkhardt, Adkins, TX (US)

(73) Assignee: Southwest Research Institute, San Antonio, TX (US)

( * ) Notice: Subject to any disclaimer, the term of this patent is extended or adjusted under 35 U.S.C. 154(b) by 7 days.

(21) Appl. No.: 11/852,247

(22) Filed: Sep. 7, 2007

(65) Prior Publication Data

US 2008/0174307 A1 Jul. 24, 2008

Related U.S. Application Data

(60) Provisional application No. 60/842,839, filed on Sep. 7, 2006.

(51) Int. Cl.
*G01N 27/82* (2006.01)

(52) U.S. Cl. ....................................... 324/240; 228/260

(58) Field of Classification Search ......... 324/228–229, 324/232, 234, 237–240, 219–221, 241–243, 324/260–263

See application file for complete search history.

(56) References Cited

U.S. PATENT DOCUMENTS 4,379,261 A 4/1983 Lakin
4,450,725 A 5/1984 Yamaguchi et al.
4,507,610 A 3/1985 Nakaoka
4,818,935 A 4/1989 Takahashi et al.
6,014,024 A 1/2000 Hockey et al.
6,404,189 B2 * 6/2002 Kwun et al. ................ 324/220
6,570,379 B2 5/2003 Crouzen et al.
6,707,297 B2 3/2004 Nath et al.
6,791,318 B2 9/2004 Paulson et al.
6,873,152 B2 3/2005 Kliman et al.
6,917,196 B2 7/2005 Kwun et al.

(Continued)

OTHER PUBLICATIONS

Moyer, M. C., Peterson, C. W., "The importance of quality tubular inspections", Oil & Gas Journal, Apr. 13, 1981, Drilling/Production; p. 103, PennWell Publishing Company.

(Continued)

*Primary Examiner*—Bot LeDynh
(74) *Attorney, Agent, or Firm*—Kammer Browning PLLC

(57) ABSTRACT

A device and methods for using the device, that permit the rapid and accurate inspection of aircraft wing attachment fittings, including those wing to fuselage attachments modified according to a Structural Life Extension Program (SLEP). Such aircraft life extension programs often result in the placement of fitting stack-up components that tend to challenge the ability of standard inspection sensors and techniques to achieve accurate readings. A specially designed, contact compliant, Electric Current Perturbation (ECP) probe is used. The ECP probe positions a receive coil in conjunction with a drive coil (and its ferrite core) in a manner that minimizes steel interferences in the inspection area. The ECP probe works with conventional eddy current instrumentation with an index scanner to allow for flaw location within a particular stack-up layer and/or within the area around the attachment aperture. Data acquired through the use of the system and method of the present invention allows for the rapid discernment of flaws and defects in the area adjacent the probe placement.

12 Claims, 5 Drawing Sheets

14
10
28
22
24
26
30
20

U.S. PATENT DOCUMENTS

2005/0237055 A1 10/2005 Sun et al.

OTHER PUBLICATIONS

Bogart, Henry G., "Modern NDT methods- express texts, no side-tracks", Production Engineering, May 1984, p. 86, vol. 31; ISSN: 0146- 1737, Penton Publishing Inc.

"Testing/inspection/measurement; of metal castings", Foundry Management & Technology, Jan. 1993, p. H2, vol. 121; No. 1; ISSN:0360-8999, Penton Publishing Inc.

Chase, Steven B.; Washer, Glenn, "Nondestructive evaluation for bridge management in the next century", Public Roads, Jul. 17, 1997, p. 16, vol. 61; No. 1; ISSN: 0033-3735, U.S. Department of Transportation.

Benoff, Dave, "NDI & T: Saving Time and Trouble", Business and Commercial Aviation, Dec. 2003, p. 82, DOM Notebook; vol. 93; No. 6, The McGraw-Hill Companies.

Devries, Dan, "Electromagnetic testing validates heat-treated part condition; Materials testing", Industrial Heating, Jan. 1, 2004, p. 39(3), vol. 71; No. 1; ISSN: 0019-8374, Business News Publishing Company.

* cited by examiner

APPARATUS AND METHOD FOR SECOND-LAYER THROUGH-BUSHING INSPECTION OF AIRCRAFT WING ATTACHMENT FITTINGS USING ELECTRIC CURRENT PERTURBATION

CROSS REFERENCE TO RELATED APPLICATIONS

This application claims the benefit under Title 35 United States Code § 119(e) of U.S. Provisional Application No. 60/842,839 filed Sep. 7, 2006, the full disclosure of which is incorporated herein by reference.

GOVERNMENT RIGHTS

The U.S. government has a paid-up license in this invention and the right in limited circumstances to require the patent owner to license others on reasonable terms as provided for by the terms of contract number F42620-00-D-0037 awarded by the Department of Defense (DOD-USAF).

BACKGROUND OF THE INVENTION

1. Field of the Invention

The present invention relates generally to devices and methods for the non-destructive inspection of structural systems. The present invention relates more specifically to devices and methods for the inspection of aircraft structural systems, particularly those associated with the attachment of a wing structure to an aircraft fuselage.

2. Description of the Related Art

Many of today's aircraft, including military aircraft, are being utilized past their original designed lifetime. This utilization creates inherent problems related to the structural limitations brought about because of the age of the aircraft. Repairs and structural modifications can extend the life of the aircraft but in the process can position structural components that affect the ability of existing test systems to perform nondestructive inspection (NDI) on areas where these modifications have been made.

An example of the above described concern is in the area of wing attachment fittings that serve to connect the wing structure to the aircraft fuselage. If a defect such as a crack is identified in an attachment fitting, the repair protocol calls for drilling or reaming out the fastener hole in the attachment fitting "stack-up area" (described in more detail below) and bushing the hole to allow for the original size fastener to be reinstalled. This procedure, however, presents an inspection problem, generally requiring the removal of the wing to gain access to the areas of interest. The process of wing removal and reinstallation is costly and not always practical given the location of the aircraft and the availability of equipment and trained personnel.

A method and a system to inspect the fastener hole of an attachment fitting stack-up without wing removal are therefore needed. Conventional NDI methods and systems are not capable of inspecting through a bushed hole with the kind of sensitivity-to-defect that is required to identify and locate flaws and defects of the size that must be identified (or confirmed absent) in order to keep the aircraft in service.

The present invention addresses the above described issues through the use of not only an inspection procedure and an inspection probe structure, but also a specific application of each. This specific application may generally be referred to as a $2^{nd}$ layer bushing inspection of an aircraft wing attachment fitting using ECP (electric current perturbation) sensing.

SUMMARY OF THE INVENTION

It is therefore an object of the present invention to provide systems and methods for the inspection of bushed fastener holes in an attachment fitting stack-up for an aircraft wing structure, which do not require wing removal. In fulfillment of this and further objectives, the present invention provides a device, and methods for using the device, that permit the rapid and accurate inspection of aircraft wing attachment fittings, including those wing to fuselage attachments modified according to a Structural Life Extension Program (SLEP). Such aircraft life extension programs often result in the placement of fitting stack-up components that tend to challenge the ability of standard inspection sensors and techniques to achieve accurate readings.

In the present invention, a specially designed, contact compliant, Electric Current Perturbation (ECP) probe is used. The ECP probe positions a receive coil in conjunction with a drive coil (and its ferrite core) in a manner that minimizes steel interferences in the inspection area. The ECP probe works with conventional eddy current instrumentation with an index scanner to allow for flaw location within a particular stack-up layer. Data acquired through the use of the system and method of the present invention allows for the rapid discernment of flaws and defects in the area adjacent the probe placement.

The methods and probe structures of the present invention therefore provide an inspection technique that allows for an accurate assessment of the integrity of an aircraft wing attachment fitting, even one that has been modified to extend its life, without the need to remove the entire wing structure from the aircraft fuselage.

DETAILED DESCRIPTION OF THE PREFERRED EMBODIMENTS

Figure 1:
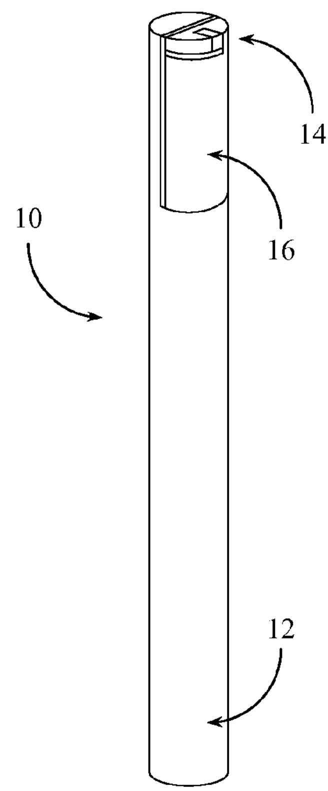
FIG. 1 is a perspective view of the assembled compliant ECP probe of the present invention.

The basis of the system and method of the present invention revolves around the design of an Electric Current Perturbation (ECP) compliant probe (see in particular FIGS. 1 and 2), capable of adjusting to the surface inside dimension of the fastener hole. This probe uses a drive coil and a differential receive coil arrangement (see in particular FIGS. 3 and 4), that significantly improve the sensor discrimination. The receive coil is advantageously positioned below the drive coil. The positioning of the receive coil to the drive coil helps minimize magnetic steel interferences of the inspection area at the receive coil by using the ferrite core of the drive coil as a shield. This arrangement increases the sensitivity to defects of the probe with both a standard attachment fitting configuration and with a Structural Life Extension Program (SLEP)-modified wing attachment fitting stack-up (see for example FIGS. 5 and 6).

In standard practice, a structural crack adjacent a fitting may be initially detected during implementation of a conventional NDI method after wing removal. The repair of such an attachment fitting hole stack-up configuration, calls for the fastener hole to be reamed or enlarged to remove the suspected crack, and a bushing to be installed, thus allowing for the original sized fastener to be reinstalled. Once bushing installation is completed, the wing is reinstalled and mated to the fuselage. Force Structural Maintenance Programs (FSMP) based on damage tolerance analysis dictate the intervals for recurring inspection. Typically, the next inspection interval would require a costly wing removal; however, through the use of the ECP probe of the present invention, a standard or SLEP-modified attachment fitting configuration could be re-inspected with only a fastener removal.

Tests conducted on a test specimen representing the stack-up area of a wing attachment fitting area (see FIGS. 7 and 8), clearly show the layers of material needing inspection after the fastener has been removed. The layers may preferably include a SLEP modification with a 17-7 ph steel addition for structural enhancement. As in the real world situation, this additional material creates problems with a conventional eddy current probe because of the magnetic interference of the steel on the receive coil. The addition and positioning of the ferrite core in association with the drive coil, with respect to the receive coil in the ECP probe (see FIG. 3) helps isolate the induced noise of the steel, thus increasing sensitivity to defects.

Data acquired using the test specimen shown and described above can be seen in FIGS. 9 and 10; both of which show the ability of the probe to detect cracks in the aluminum skin layer even when positioned next to the 17-7 ph steel layer. As can be seen in the aforementioned figures, the probe of the present invention can detect flaws in the skin when positioned closest to the steel and furthest from the steel. Although the magnetic interferences from the steel can be seen in the upper region of both graph figures, with the shielding effect of the drive coil's ferrite core, the interference is reduced enough to allow for the detection of the cracks.

The ECP probe design of the present invention, with the drive coil and receive coil arrangement described, allows for sensitivity to small defects in aluminum skin with a repaired, bushed, fastener hole when positioned next to a steel strap in an SLEP-modified wing attachment fitting configuration.

In addition, the ECP probe design of the present invention, with the drive coil and receive coil arrangement described, also allows for sensitivity to small defects in aluminum skin with a repaired, bushed, fastener hole in a standard wing attachment fitting configuration.

The ECP probe of the present invention works with conventional eddy current instrumentation with an indexing scanner. This allows for an inspector to verify flaw location within the particular stack-up layer.

Finally, the unique compliant probe design, with its integrated spring mechanism, maintains the surface of the probe face in contact with the inside dimension wall of the attachment fitting fastener hole. As a result of this compliant contact, the data acquired allows for the discrimination of flaw information outside of the interference caused by added structural components.

Reference is made to FIG. 1 for a brief description of the overall structure of the compliant Electric Current Perturbation (ECP) probe 10 of the present invention. The size and shape of probe 10 is generally that of the fastener used to attach the wing to the fuselage of the aircraft. The generally cylindrical probe 10 has a handle end 12 and a sensor end 14. Positioned on the sensor end 14 is a proximity compliance mechanism 16 that serves to assure sufficient signal transmission proximity to the wall of the fastener hole being investigated.

Figure 2:
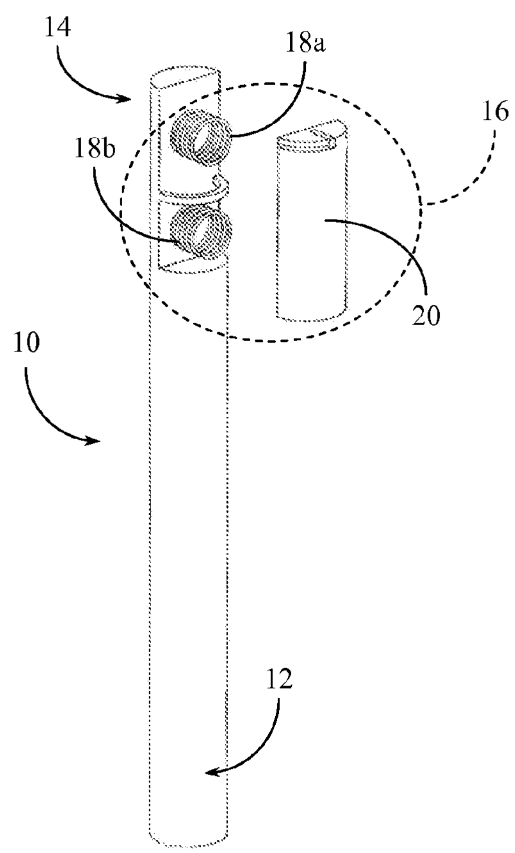
FIG. 2 is a partially exploded perspective view of the compliant ECP probe of the present invention.

FIG. 2 discloses the same ECP probe 10 in a partially exploded view, wherein the compliant mechanism 16 is segregated into its functional components as part of the sensor end 14 of the probe. In this view, compliant spring mechanisms **18*a* and 18*b* are shown positioned in a manner such that they preference sensor contact face 20** against the interior wall of the fastener hole to be investigated. The manner in which the sensor elements of the probe investigate the structures within the fastener aperture is described in more detail below. It will be understood by those skilled in the art that the necessary electrical signal connections for the probe (omitted for clarity in these views) would extend from the probe in the vicinity of the handle end, to connect to the appropriate instrumentation for the inspection system.

Figure 3:
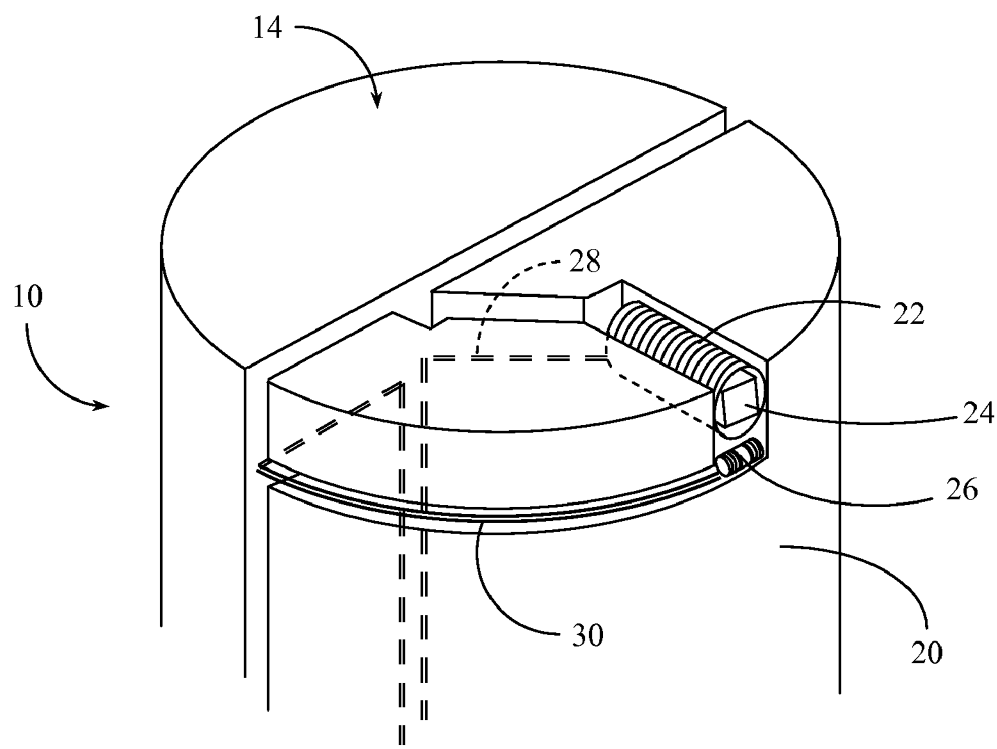
FIG. 3 is a detailed perspective view of the sensor components of the ECP probe of the present invention.

FIG. 3 is a detailed view of the sensor end 14 of ECP probe 10. At this end of the probe, sensor contact face 20 is shown to incorporate the various electrical/electronic components (coils) that make up the sensor structure of the probe. At the sensor end 14 of sensor contact face 20 are positioned drive coil 22 (which surrounds ferrite core 24) and differential receive coil 26. Drive coil connection conductors 28 extends from drive coil 22 through interior channels within probe 10 to a point where they extend lengthwise, interior to the probe 10, towards the handle end 12 of the probe. In similar fashion, receive coil connection conductors 30 extend from differential receive coil 26 in a direction apart from drive coil 22 again to a point where they extend down along the length of the probe interior toward the handle end 12 of the probe 10.

As mentioned, the above described probe structure allows for an appropriate level of shielding to occur over differential receive coil 26. The ferrite core 24 and drive coil 22 positioned adjacent to differential receiver coil 26 provide the necessary shielding to reduce the effects of the steel plate components of the inspected structures, which steel components are typically placed as part of a SLEP-modified wing attachment fitting configuration.

Figure 4:
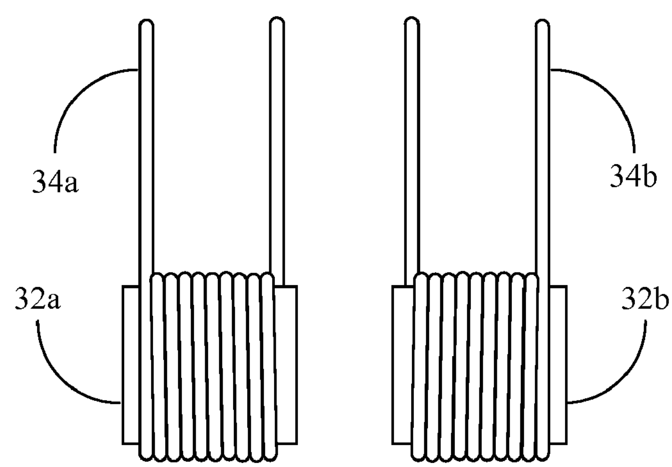
FIG. 4 is a detailed plan view of the differential receive coil component of the ECP probe of the present invention.

Reference is now made briefly to FIG. 4 for a detailed view of the differential receive coil structure of the present invention. The differential receive coils are, as known in the art, counter wound coils positioned coaxial with each other. In this view of FIG. 4, receive coil core **32*a* is wound in a clockwise direction (when viewed from the left looking towards the right in FIG. 4) by way of receive coil windings 34***a*. In similar but opposite fashion, receive coil core 32*b* is counter wound (counter clockwise in the view mentioned above) with receive coil windings 34*b*. With this structure, differential receive coil 26 operates to detect a return signal from the material initiated by the drive coil as is known in the art.

Figure 5:
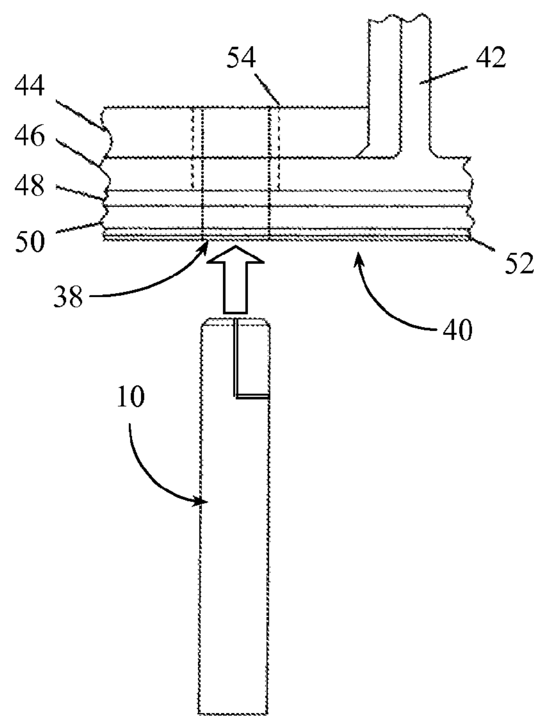
FIG. 5 is a detailed partial cross sectional view showing the probe of the present invention utilized in conjunction with a fastener hole on a typical wing structure.
Figure 6:
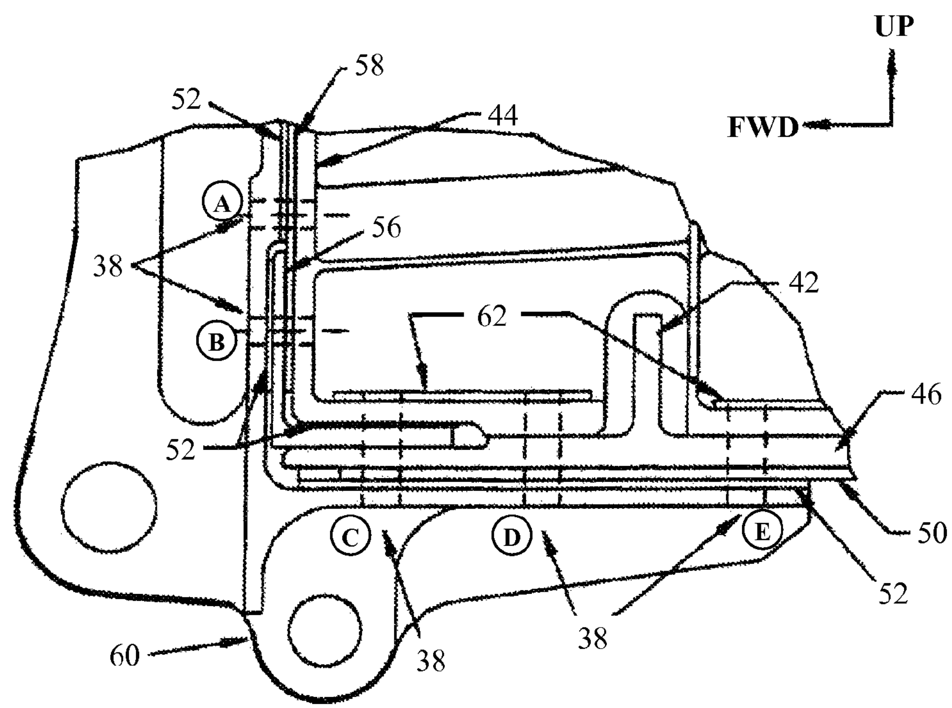
FIG. 6 is a detailed partial cross sectional view of a wing structure bearing five (5) fastener holes appropriate for use in conjunction with the probe and system of the present invention.

Reference is now made to FIGS. 5 and 6 for a brief description of the manner in which ECP probe 10 is utilized in conjunction with the inspection of fastener hole apertures associated with the attachment of a wing to an aircraft fuselage. In FIG. 5 a detailed view of the area and structure immediately surrounding fastener hole 38 is shown. Probe 10 is shown positioned for insertion into fastener hole 38, which is itself positioned on wing structure 40. The wing is structured to include stringer 42 (as an example) and rib 44 (as an example) in the manner shown in FIG. 5 which is typical for the environment surrounding a wing attachment fastener hole 38. Immediately adjacent and overlaying rib 44 is lower skin 46. Outside of lower skin 46 is SLEP strap 48 placed and positioned as described above. Overlaying SLEP strap 48 is Longeron splice fitting 50. Overlaying Longeron splice fitting 50 are a number of shims 52. Bushing 54 is shown positioned within fastener hole 38 as a retrofit for the purpose of extending the life of the aircraft structure.

FIG. 6 shows (in partial cross sectional detail) a number of fastener holes 38 (labeled A through E in FIG. 6). The partial cross sectional view shown in FIG. 5 may be recognized as a portion of the view shown in FIG. 6 associated with fastener hole D as an example. In addition to the above mentioned structures associated with lower skin 46, SLEP strap 48, Longeron splice fitting 50, and the various shims 52, the view shown in FIG. 6 additionally discloses the placement of front spar web 58 as well as front spar cap 56. Associated with a number of fastener holes 38 on the interior of the wing structure 40 are radius blocks 62. A primary wing fuselage fitting 60 is also disclosed in this view. In this detail shown in FIG. 6 it can be seen how the individual and sequential use of probe 10 progressively through each of the fastener holes 38 can readily accomplish an inspection of these fittings associated with the attachment system.

Figure 7:
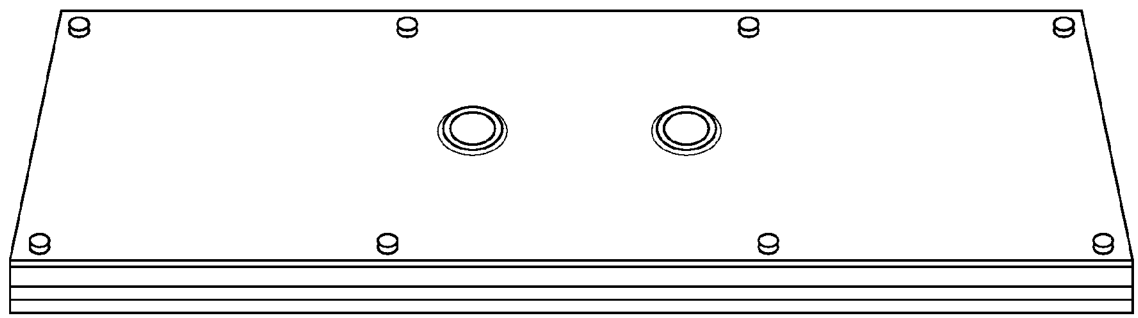
FIG. 7 is a perspective view of a simulated wing attachment fitting utilized as a test specimen for use in conjunction with the present invention.
Figure 8:
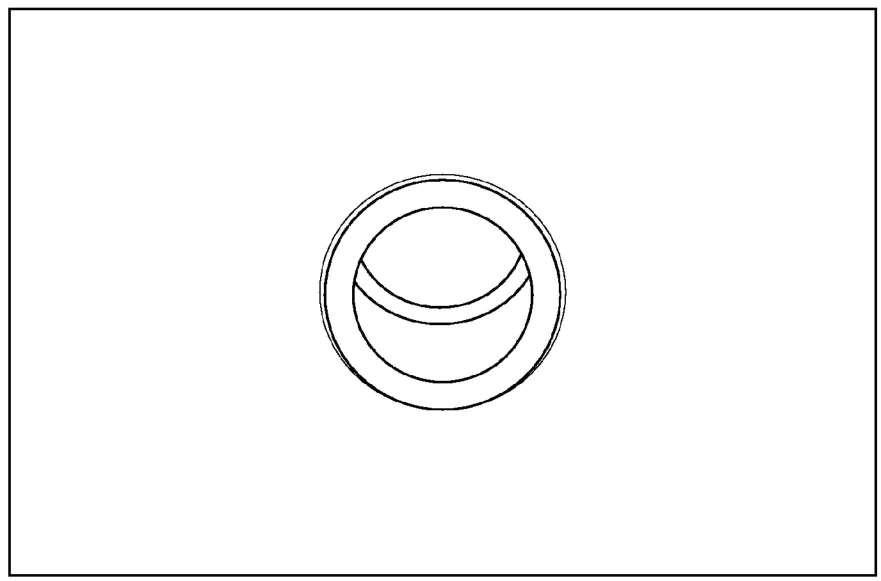
FIG. 8 is a detailed perspective view of a simulated inspection hole representing a typical fastener hole for a wing structure applicable to the present invention.

A bench test set up appropriate for confirmation of the functionality of the probe and the associated methodology of the present invention is shown in the views presented in FIGS. 7 and 8. FIG. 7 represents a test set up, descried briefly above, designed to accurately represent the stack up area of a wing attachment fitting system as the same might appear after a fastener has been removed. The layers of material in the assembly include a SLEP modification with a 17-7 small ph steel addition for structural enhancement. FIG. 8 is a close up detailed view of one the fastener apertures on the test specimen set up.

Figure 9:
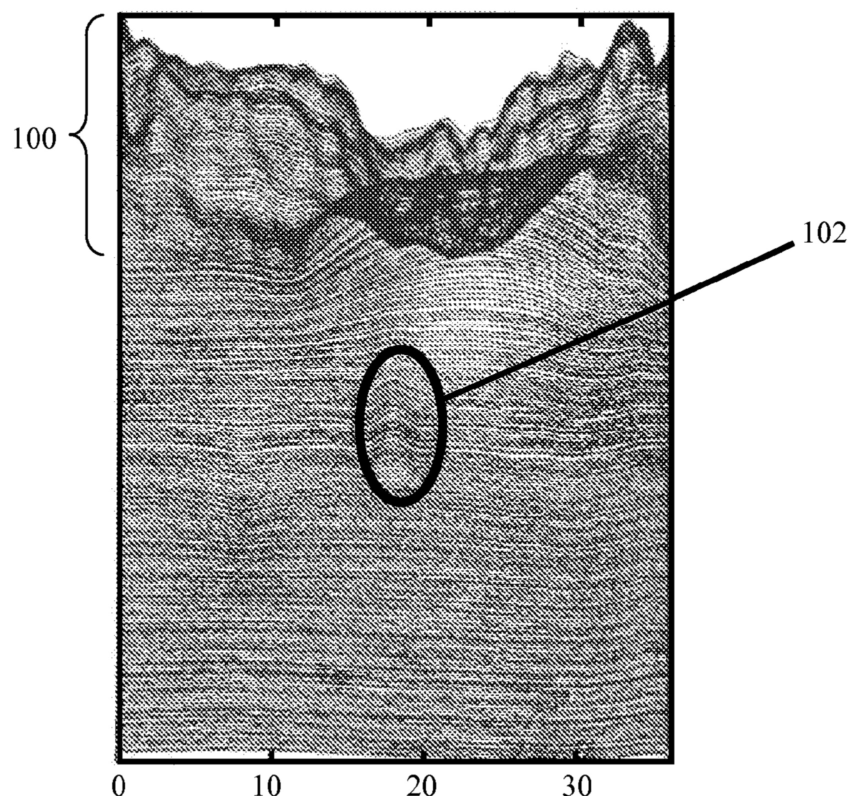
FIG. 9 is a graphic plot of data collected with the system of the present invention showing evidence of a detected flaw furthest from the interfering steel.
Figure 10:
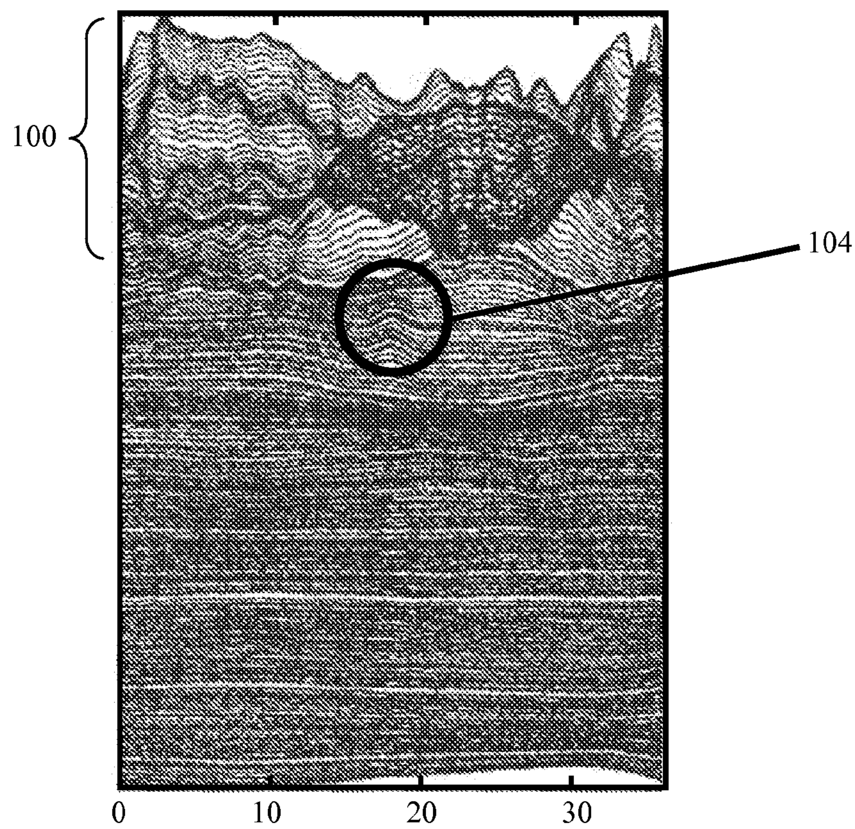
FIG. 10 is a graphic plot of data collected with the system of the present invention showing evidence of a detected flaw closest to the interfering steel.

FIG. 9 as described briefly above, comprises test data results showing evidence of a crack 102 positioned furthest from the steel addition in the assembly. In this case the crack is a 0.095 inch×0.050 inch flaw positioned furthest from the steel component in the area adjacent the aperture. FIG. 10 displays a similar set of data showing a 0.095 inch×0.050 inch flaw positioned closest to the steel component. In each case, the graphic data shown in FIGS. 9 and 10 includes evidence of magnetic interferences from the steel component, which can be seen in the top portion of both figures in range 100 on the vertical graphic scale. As indicated above, due to the shielding effect provided by the drive coil ferrite core, this interference is reduced enough to readily permit the detection of signal data associated with the flaws in the area under investigation.

Although the present invention has been described in terms of the foregoing preferred embodiments, this description has been provided by way of explanation only, and is not intended to be construed as a limitation of the invention. Those skilled in the art will recognize modifications of the present invention that might accommodate specific environments and specific aircraft fitting geometries. Such modifications as to size, and even configuration, where such modifications are merely coincidental to the specific application of the devices and methods, do not necessarily depart from the spirit and scope of the invention.

We claim:

1. An electric current perturbation (ECP) probe for detecting anomalies in a structure surrounding a fitting aperture, the ECP probe comprising:

(a) a probe body sized and structured for insertion into the fitting aperture to maintain contact with an interior wall of the aperture, the probe body generally cylindrical in configuration and having a handle end and a sensor end;

(b) a compliant mechanism positioned on the probe body at the sensor end thereof, the compliant mechanism comprising a sensor contact element and an expansion element, the expansion element preferencing the sensor contact element against the interior wall of the aperture upon insertion of the probe into the aperture; and (c) an ECP sensor system positioned on the sensor contact element of the compliant mechanism, the ECP sensor system comprising a drive coil with a ferrite core and a differential receive coil.

2. The probe of claim 1 wherein the differential receive coil is positioned adjacent the drive coil and ferrite core in a manner that shields the receive coil from extraneous interferences.

3. The probe of claim 1 further comprising electrical current conductors extending to the drive coil, and electrical signal conductors extending from the differential receive coil.

4. The probe of claim 3 wherein the sensor contact element comprises an array of recessed channels for directing the electrical current conductors and the electrical signal conductors away from the sensor contact element without interfering with the fit of the probe into the fitting aperture.

5. An electric current perturbation (ECP) probe for detecting anomalies in a structure surrounding a fitting aperture, the ECP probe comprising:

(a) a probe body sized and structured for insertion into the fining aperture to maintain contact with an interior wall of the aperture, the probe body generally cylindrical in configuration and having a handle end and a sensor end;

(b) a compliant mechanism positioned on the probe body at the sensor end thereof, the compliant mechanism comprising a sensor contact element and an expansion element, the sensor contact element comprising a cylindrical section movable in a direction generally orthogonal to a long axis of the probe, and the expansion element preferencing the sensor contact element against the interior wall of the aperture upon insertion of the probe into the aperture, the expansion element comprising at least one spring positioned and compressed between the sensor contact element and the balance of the sensor end of the probe body; and (c) an ECP sensor system positioned on the sensor contact element of the compliant mechanism, the ECP sensor system comprising a drive coil with a ferrite core and a differential receive coil, the differential receive coil positioned adjacent the drive coil and ferrite core in a manner that shields the receive coil from extraneous interferences.

6. A method for the inspection of aircraft structural component attachment fittings, the method capable of being carried out without the necessity of removing the aircraft structural components from each other, the method comprising:

(a) removing, one at a time and in turn, each of a plurality of fasteners associated with the attachment fittings between the structural components, the removal of the fastener exposing a fitting aperture;

(b) providing a compliant electric current perturbation (ECP) probe, the probe comprising a compliant mechanism positioned on a probe body for preferencing a probe sensor element against an interior wall of the fitting aperture;

(c) inserting the ECP probe into the fitting aperture so as to establish compliant contact between the probe sensor element and the interior wall of the aperture;

(d) providing an interrogation drive signal to the ECP probe sensor element;

(e) receiving a return signal from the ECP probe, the return signal containing signal characteristics indicative of a presence or absence of anomalies in a structural area surrounding the fitting aperture; and (f) discriminating an anomaly signal from interference components of the return signal, wherein the discrimination of the anomaly signal characteristics is facilitated by shielding the probe sensor element.

7. The method of claim 6 wherein the step of providing an ECP probe further comprises providing a drive coil/core and a receive coil on the probe sensor element, the receive coil positioned on the probe sensor element in a manner such that the drive coil/core shields the receive coil from extraneous interferences.

8. The method of claim 6 wherein the fitting aperture has previously been configured with a bushing therein and the ECP probe is sized and structured to be inserted into the bushed fitting aperture.

9. The method of claim 6 wherein the use of the ECP probe is carried out in conjunction with eddy current signal instrumentation.

10. The method of claim 6 wherein the use of the ECP probe is carried out in conjunction with eddy current instrumentation and an indexing scanner system.

11. The method of claim 6 wherein the step of inserting the ECP probe comprises compressing an expandable sensor element of the probe, positioning the probe into the fitting aperture, and allowing the expansion of the expandable sensor element of the probe so as to establish compliant contact between the probe sensor element and the interior wall of the aperture.

12. A method for the inspection of aircraft structural component attachment fittings, the method capable of being carried out without the necessity of removing the aircraft structural components from each other, the method comprising:

(a) removing, one at a time and in turn, each of a plurality of fasteners associated with the attachment fittings between the structural components, the removal of the fastener exposing a fitting aperture;

(b) providing a compliant electric current perturbation (ECP) probe, the probe comprising a compliant mechanism positioned on a probe body for preferencing a probe sensor element against an interior wall of the aperture, the ECP probe further comprising a drive coil/core and a receive coil, the receive coil positioned in a manner such that the drive coil/core shields the receive coil from extraneous interferences;

(c) inserting the ECP probe into the fitting aperture so as to establish compliant contact between the probe sensor element and the interior wall of the aperture;

(d) providing an interrogation drive signal to the drive coil/core of the ECP probe;

(e) receiving a return signal with the receive coil of the ECP probe, the return signal containing signal characteristics indicative of a presence or absence of anomalies in a structural area surrounding the fitting aperture; and (f) discriminating an anomaly signal from interference components of the return signal, wherein the discrimination of the anomaly signal characteristics is facilitated by shielding the probe sensor element.

* * * * *